US010545156B2

(12) United States Patent
Equils et al.

(10) Patent No.: US 10,545,156 B2
(45) Date of Patent: Jan. 28, 2020

(54) DIAGNOSTIC BIOMARKER TO PREDICT WOMEN AT RISK FOR PRETERM DELIVERY

(71) Applicant: RPI CONSULTING LLC, Encino, CA (US)

(72) Inventors: Ozlem Equils, Sherman Oaks, CA (US); Charles F. Simmons, Los Angeles, CA (US)

(73) Assignee: RPI Consulting, LLC, Encino, CA (US)

( * ) Notice: Subject to any disclaimer, the term of this patent is extended or adjusted under 35 U.S.C. 154(b) by 518 days.

(21) Appl. No.: 14/946,454

(22) Filed: Nov. 19, 2015

(65) Prior Publication Data

US 2016/0077102 A1 Mar. 17, 2016

Related U.S. Application Data

(63) Continuation of application No. 14/003,334, filed as application No. PCT/US2012/028934 on Mar. 13, 2012, now abandoned.

(60) Provisional application No. 61/453,765, filed on Mar. 17, 2011.

(51) Int. Cl.
G01N 33/68 (2006.01)

(52) U.S. Cl.
CPC ....... *G01N 33/689* (2013.01); *G01N 33/6863* (2013.01); *G01N 33/6866* (2013.01); *G01N 33/6869* (2013.01); *G01N 2800/368* (2013.01)

(58) Field of Classification Search
None
See application file for complete search history.

(56) References Cited

U.S. PATENT DOCUMENTS

| 5,545,616 | A | 8/1996 | Woodruff et al. |
| 7,232,661 | B2 | 6/2007 | Yoon et al. |
| 7,790,463 | B2 | 9/2010 | Mor et al. |
| 7,892,774 | B2 | 2/2011 | Rutanen |
| 2001/0034037 | A1* | 10/2001 | Patel .................. G01N 33/5091 435/7.21 |
| 2004/0014063 | A1 | 1/2004 | Batteux et al. |
| 2006/0063162 | A1 | 3/2006 | Deng |
| 2006/0166277 | A1 | 7/2006 | Karumanchi et al. |
| 2007/0161125 | A1 | 7/2007 | Rosenfeld et al. |
| 2007/0178605 | A1 | 8/2007 | Mor et al. |
| 2007/0238655 | A1 | 10/2007 | Bucki et al. |
| 2009/0226397 | A1 | 9/2009 | Carter |
| 2010/0137263 | A1 | 6/2010 | Smith |
| 2012/0238469 | A1 | 9/2012 | Equils et al. |
| 2014/0051598 | A1 | 2/2014 | Equils et al. |
| 2016/0069891 | A1 | 3/2016 | Equils et al. |
| 2018/0038871 | A1 | 2/2018 | Equils et al. |

FOREIGN PATENT DOCUMENTS

| AU | 2012230065 B2 | 11/2015 |
| AU | 2015249071 B2 | 2/2018 |
| EP | 2510356 | 10/2012 |
| EP | 2686681 | 1/2014 |
| WO | 94/28425 A1 | 12/1994 |
| WO | WO 07/112514 | 10/2007 |
| WO | WO 08/056114 | 5/2008 |
| WO | WO 09/134452 | 11/2009 |
| WO | WO 11/071893 | 6/2011 |
| WO | 2012125641 A1 | 9/2012 |

OTHER PUBLICATIONS

Menon et al. (2011) "Biomarkers of Spontaneous Preterm Birth: An Overview of the Literature in the Last Four Decades" Reproductive Sciences 18(11):1046-1070.*
Wei et al. (2010) "Inflammatory Cytokines and Spontaneous Preterm Birth in Asymptomatic Women" Obstetrics and Gynecology 116(2):393-401.*
Thurm et al. (2005) "Measurement of cytokine production using whole blood." Curr Protoc Immunol. Chapter 7:Unit 7. 18B.*
Hossein et al (2004) "Cytokine production by peripheral blood mononuclear cells in recurrent miscarriage" Cytokine 28(2):83-86.*
Matalka et al (2005) "Kinetics and functional implications of Th1 and Th2 cytokine production following activation of peripheral blood mononuclear cells in primary culture" Neuroimmunomodulation 12(6):366-74.*
Kruse et al. (2003) "Prospective, serial investigations of in-vitro lymphocyte cytokine production, CD62L expression and proliferative response to microbial antigens in women with recurrent miscarriage" Human Reproduction 18(11):2465-2472.*
Romero et al. (1994) "The natural interleukin-1 receptor antagonist in the fetal, maternal, and amniotic fluid compartments: the effect of gestational age, fetal gender, and intrauterine infection." American Journal of Obstetrics and Gynecology 171(4):912-921. Abstract Only.*
Curry et al., 2009, "First-trimester plasma cytokine levels, pre-pregnancy body mass index, and spontaneous preterm delivery," Acta Obstet Gynecol Scand. ePub 88:332-42.
Kalinka et al., 2008, "Interleukin-1beta and interleukin-1 receptor antagonist gene polymorphisms and the risk of spontaneous preterm delivery in the population of Polish women," Arch Perinatal Med. 14(4):33-36.
Bussen et al., 1995, "Thyroid autoantibodies in euthyroid non-pregnant women with recurrent spontaneous abortions," Human Reproduction 10(11): 2938-2940.

(Continued)

*Primary Examiner* — Karen S. Weiler
(74) *Attorney, Agent, or Firm* — Torrey Pines Law Group

(57) ABSTRACT

The invention relates to biomarkers associated with preterm delivery. More specifically, the invention provides methods of measuring biomarkers including but not limited to cytokines, cytokine receptors, cytokine receptor antagonists, chemokines, chemokine receptors, and/or chemokine receptor antagonists found in women that are at risk for preterm delivery. The diagnostic methods may be performed on whole blood.

8 Claims, 2 Drawing Sheets

(56) References Cited

OTHER PUBLICATIONS

Skogstrand et al., 2005, "Simultaneous measurement of 25 inflammatory markers and neurotrophins in neonatal dried blood spots by immunoassay with xMAP technology," Clin. Chem. 51(10):1854-66.
Romero et al., 1992, "The natural interleukin-1 receptor antagonist prevents interleukin-1 induced preterm delivery in mice," Am. J. Obstet. Gynecol. 167(4)(1):1041-5.
Hollier et al., 2004, "T helper cell cytokine profiles in preterm labor," American Journal of Reproductive Immunology, 52:192-196.
Hamano et al., 1998, "Effect of female hormones on the production of IL-4 and IL-13 from peripheral blood mononuclear cells," Acta Otolaryngolgica. Supplementum 537:27-31.
Schaub et al., 2004, "TLR2 and TLR4 stimulation differentially induce cytokine secretion in human neonatal, adult, and murine mononuclear cells," Journal of Interferon & Cytokine Research, 24:543-552.
Cesario et al., 1986, "The effect of hydrocortisone on the production of gamma-interferon and other lymphokines by human peripheral blood mononuclear cells," Journal of Interferon Research, 6:337-347.
Amory et al., 2001, "Increased Tumor Necrosis Factor-a Production," Am J. Obstet. Gynecol., 185(5):1064-1067.
Makhseed et al., 2003, "Pro-inflammatory Maternal Cytokine Profile in Preterm Delivery," Amer. J. Repro. Immunol., 49:308-318.
Schlafer et al., 1994, "Effect of Salmonella Endotoxin Administered to the Pregnant Sheep," Biol. of Repro., 50:1297-1302.
Robertson et al., 2006, "Essential Role for IL-10 in Resistance to Lipopolysaccharide-Induced Preterm Labor in Mice," J. Immunol., 177:4888-4896.
Menon et al., 2006, "Difference in the Placental Membrane Cytokine Response: A Possible Explanation for Racial Disparity," Am. J. Reprod. Immunol., 56:112-118.
Marzi et al., 1996 "Characterization of type 1 and type 2 cytokine production profile in physiologic and pathologic human pregnancy," Clinical & Experimental Immunology, 106(1):127-133.
Wetta et al., 2008, "168: Impaired anti-inflammatory response in women with a prior spontaneous preterm birth," American Journal of Obstetrics and Gynecology, 199(6):S59.
International Preliminary Report on Patentability dated Jun. 12, 2012 in connection with International Application No. PCT/US2010/059248.
International Search Report dated Apr. 12, 2011 in connection with International Application No. PCT/US2010/059248.
Supplementary European search report and European search opinion dated Apr. 10, 2013 in connection with European application No. 10836527.1.
Office Action dated Feb. 27, 2015 in connection with U.S. Appl. No. 13/512,212.
International Search Report dated Jul. 2, 2012 in connection with International Application No. PCT/US2012/28934.
International Preliminary Report on Patentability dated Sep. 17, 2013 in connection with International Application No. PCT/US2012/028934.
Supplementary European search report and European search opinion dated Nov. 24, 2014 in connection with European application No. 12757314.5.
Written Opinion of PCT/US2012/028934, dated Sep. 17, 2013, 8 Pages.
Aguilar-Valles et al., Attenuated Fever in Rats during Late Pregnancy is Linked to Suppressed Interleukin-6 Production after Localized Inflammation with Turpentine, 2007, Journal of Physiology, vol. 583(Pt. 1), pp. 391-401.
Bates et al., Aberrant Cytokine Production by Peripheral Blood Mononuclear Cells in Recurrent Pregnancy Loss?, 2002, Human Reproduction, vol. 17(9), pp. 2439-2444.
Fofie et al., Pregnancy Influences the Plasma Cytokine Response to Response to Intraperitoneal Administration of Bacterial Endotoxin in Rats, 2004, Experimental Physiology, vol. 90(1), pp. 95-101.
Fujiwaki et al., Clinical Significance of Interleukin-1 Receptor Antagonist in Patients with Cervical Carcinoma, 2003, Gynecologic Oncology, vol. 89, pp. 77-83.
Lok et al., Leukocyte Activation and Circulating Leukocyte-Derived Microparticles in Preeclampsia, 2009, American Journal of Reproductive Immunology, 2009, vol. 61, pp. 346-359.
Maes et al., Immune Activation in the Early Puerperium is Related to Postpartum Anxiety and Depressive Symptoms, 2000, Psychoneuroendocrinology, vol. 25, pp. 121-137.
Pepe et al., Limitations of the Odds Ratio in Gauging the Performance of a Diagnostic, Prognostic, or Screening Marker, 2004, American Journal of Epidemiology, vol. 159(9), pp. 882-890.
Ralston et al., Estrogen Inhibits Release of Tumor Necrosis Factor from Peripheral Blood Mononuclear Cells in Postmenopausal Women, 1990, Journal of Bone and Mineral Research, vol. 5(9), pp. 983-988.
Vassiliadis et al., Serum Levels of Pro- and Anti-Inflammatory Cytokines in Non-Pregnant Women, During Pregnancy, Labour and Abortion, 1998, Mediators of Inflammation, vol. 7, pp. 69-72.

\* cited by examiner

*Significant difference between similarly treated preterm group (p < 0.10)

*Significant difference between similarly treated preterm group (p < 0.10)

DIAGNOSTIC BIOMARKER TO PREDICT WOMEN AT RISK FOR PRETERM DELIVERY

CROSS-REFERENCE TO RELATED APPLICATIONS

This application is a continuation of U.S. application Ser. No. 14/003,334, which is a national stage application of International Application No. PCT/US12/28934, filed Mar. 13, 2012, the contents of which are incorporated by reference herein in their entireties. International Application No. PCT/US12/28934 claims the benefit of the filing date of U.S. Provisional Application No. 61/453,765, filed Mar. 17, 2011.

FIELD OF INVENTION

This invention relates to preterm delivery. More specifically, the invention provides biomarkers and methods of using biomarkers for determining preterm delivery risk.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Preterm delivery is one of the most important fetal health problems in the United States today. Approximately one in eight newborns is delivered preterm and the incidence of prematurity has not decreased in the last 20 years. Most preterm babies, if they survive, often have cardiac, neurologic, ophthalmic, and gastrointestinal problems that can extend even beyond childhood, and perhaps lead to adult diseases such as atherosclerosis. Currently, there are few, if any diagnostic biomarkers available that effectively identify women who are going to deliver preterm. Biomarkers that are able to identify these women at risk would be useful in the deployment of prevention/treatment strategies and to assess the effectiveness of these treatments. Thus, there is a need to develop novel diagnostics that may identify women who will deliver preterm. Especially, diagnostic biomarkers that may be detected in non-pregnant women or in women during the first trimester. The biomarkers may also be used later in the pregnancy to assess the effectiveness of treatment and/or prevention strategies.

SUMMARY OF THE INVENTION

The following embodiments and aspects thereof are described and illustrated in conjunction with compositions and methods which are meant to be exemplary and illustrative, not limiting in scope.

Various embodiments of the present invention provides for a method, comprising: obtaining a biological sample from a woman who desires an assessment of her risk for preterm delivery; exposing the biological sample ex vivo to an antigen and/or a stimulant; and assessing an immune response to predict whether the woman is at risk for preterm delivery. In various embodiments, the biological sample can be whole blood.

In various embodiments, the method can further comprise separating blood cells from the sample and exposing the separated blood cells to the antigen.

In various embodiments, exposing the biological sample ex vivo to the antigen or the stimulant can be by collecting the biological sample into a container coated with the antigen and/or stimulant.

In various embodiments, the method can further comprise removing plasma from the biological sample and assaying the plasma to assess the immune response. In various embodiments, removing plasma from the biological sample can comprise centrifuging the tube comprising the biological sample and harvesting the plasma.

In various embodiments, the antigen and/or stimulant can be cortisol, LPS, phytohemagglutinin, a maternal histocompatibility antigen, a paternal histocompatibility antigen, a fetal histocompatibility antigen, a microbial antigen, a cytokine, a phorbol ester, an agent capable of inducing Th1 or Th2 type differentiation of lymphocytes or combination thereof.

In various embodiments, assessing the immune response can comprise assaying an expression level of a cytokine, cytokine receptor, cytokine receptor antagonist, chemokine, chemokine receptor, chemokine receptor antagonist, or combinations thereof. In various embodiments, the cytokine, cytokine receptor, cytokine receptor antagonist, chemokine, chemokine receptor, chemokine receptor antagonist, or combinations thereof can be selected from the group consisting of IL-10, IL-13, IL-1RA and combinations thereof.

In various embodiments, a higher or lower expression level of the cytokine, cytokine receptor, cytokine receptor antagonist, chemokine, chemokine receptor, and/or chemokine receptor antagonist compared to a control can indicate that the woman is at an increased risk of preterm delivery. In various embodiments, the higher or lower expression level of the cytokine, cytokine receptor, cytokine receptor antagonist, chemokine, chemokine receptor, and/or chemokine receptor antagonist can be at least one to three times higher or lower compared to the levels of the control. In various embodiments, the level of the higher or lower expression of the cytokine, cytokine receptor, cytokine receptor antagonist, chemokine, chemokine receptor, and/or chemokine receptor antagonist can be indicative of a low, medium, or high risk of preterm delivery. In various embodiments, a statistically significantly higher or lower expression of the cytokine, cytokine receptor, cytokine receptor antagonist, chemokine, chemokine receptor, and/or chemokine receptor antagonist compared to a control can indicate that the woman is at an increased risk of preterm delivery.

In various embodiments, assessing the immune response can comprise using a technique selected from the group consisting of enzyme-linked immunosorbent spot (ELISpot), enzyme-linked immunosorbent assay (ELISA), microarray assay, quantitative BCP, Northern blot assay, Southern blot assay, Western blot assay, immunohistochemical assay, binding assay and combinations thereof.

Various embodiments provide for a kit, comprising: a container comprising an antigen and/or a stimulant; instructions to use the container to collect a biological sample from a woman to detect an immune response; and instructions to determine the risk of preterm delivery of the woman. In various embodiments, the kit can further comprise a reagent to detect the immune response. In various embodiments, the kit can further comprise a positive control and/or a negative control.

Various embodiments provide for a method, comprising: obtaining a sample of whole blood from a woman who desires an assessment of her risk for preterm birth; exposing the sample ex vivo to an antigen and/or a stimulant by collecting the sample into a container coated with the antigen and/or stimulant; and assessing an immune response to predict whether the woman is at risk for preterm birth. In various embodiments, the antigen and/or stimulant can be cortisol, LPS, phytohemagglutinin, or combinations thereof. In various embodiments, assessing the immune response can comprise assaying an expression level of a cytokine, cytokine receptor, cytokine receptor antagonist, chemokine, chemokine receptor, chemokine receptor antagonist, or combinations thereof, wherein a statistically significantly higher or lower expression level of the cytokine, cytokine receptor, cytokine receptor antagonist, chemokine, chemokine receptor, and/or chemokine receptor antagonist compared to a control indicates that the woman is at an increased risk of preterm delivery. In various embodiments, the cytokine, cytokine receptor, cytokine receptor antagonist, chemokine, chemokine receptor, chemokine receptor antagonist, or combinations thereof can be selected from the group consisting of IL-10, IL-13, IL-1RA and combinations thereof.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1A:
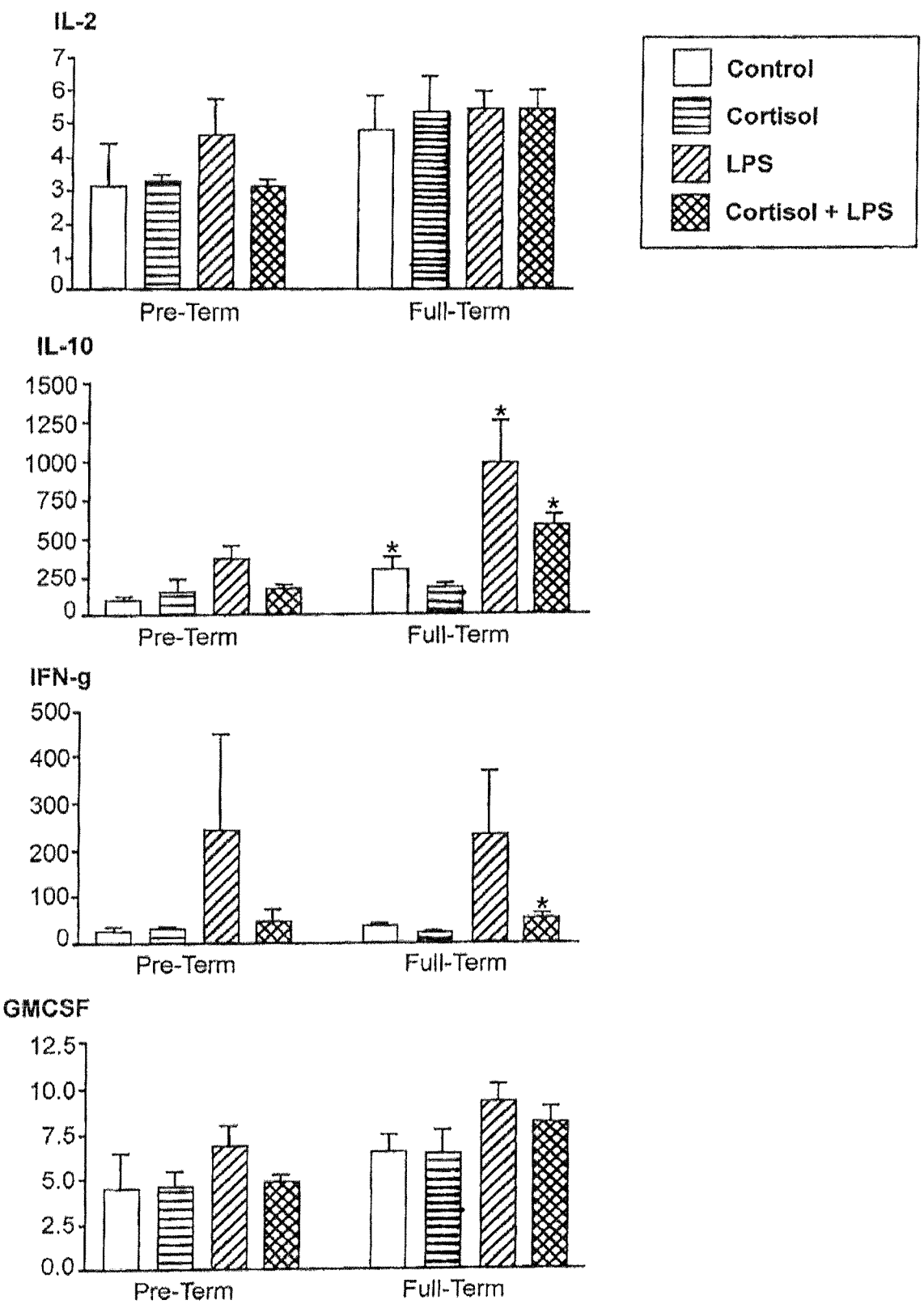
FIGS. 1A and 1B depict graphical representation of expression levels of various biomarkers of preterm individuals as compared to full term individuals in accordance with various embodiments of the present invention. Empirical means and standard errors for each cytokine and treatment group are presented.
Figure 1B:
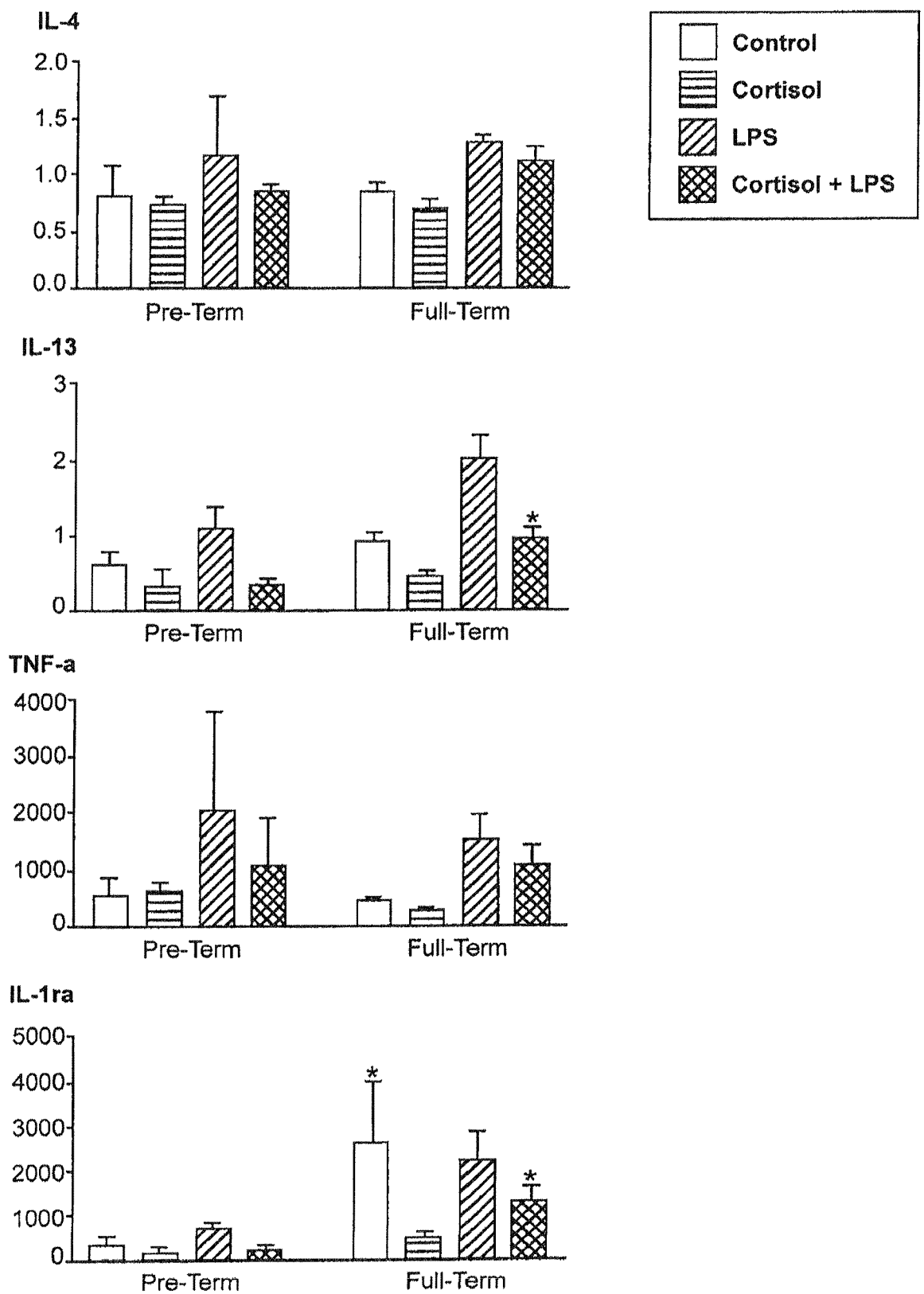

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

Multiple factors lead to preterm delivery; however, immune activation is thought be the final effector pathway that leads to preterm rupture of membranes and contractions. Family and genetic studies suggest that prematurity runs in families and history of prior preterm delivery increases the risk of future preterm deliveries. The inventors believed that these observations can be explained by the inherent differences in the immune responses of women who deliver preterm compared with those who deliver full term, and that these differences can be detected even in the non-pregnant state. The inventors believed that by detecting these differences one may be able to identify those women who are at risk to deliver preterm even before they become pregnant. The inventors believed that in order to see the differences, the immune cells of the patient had to be stressed.

The inventors are the first to have discovered a biomarker assay that provides physicians with a tool to identify women who are at risk for preterm delivery, even before they become pregnant or while pregnant, using a nonspecific immunologic test. Identification of women at risk allows the physician to better focus on preventative strategies in these women and improve pregnancy outcome. In one embodiment, the test may be done on small amounts of blood sample obtained from the subject, thus being minimally invasive to the fetus. The blood may be drawn directly into a test tube coated with a stimulant; alternatively the blood may be sent to a laboratory to be processed and stimulated in the laboratory. Furthermore, the test may be repeated multiple times during the course of pregnancy. Thus, it provides dynamic assessment of the preterm delivery risk under the influence of changing environmental/physiologic factors, as wells as requires minimal skills to draw blood as opposed to obtaining amniotic fluid.

One skilled in the art will recognize many methods and materials similar or equivalent to those described herein, which could be used in the practice of the present invention. The present invention is in no way limited to the methods and materials described. For purposes of the present invention, the following terms are defined below.

As used herein, the term "preterm delivery" refers to a premature birth or conditions associated with a premature birth, including for example, a child delivered before 34 weeks of gestation.

"Biomarker," "diagnostic biomarker," or "preterm delivery biomarker" refers to a molecular indicator that is associated with a particular pathological or physiological state. The "biomarker" as used herein is an indicator for risk of preterm delivery. The indicator can be a cytokine, cytokine receptor, cytokine receptor antagonist, chemokine, chemokine receptor, chemokine receptor antagonist or an immunomodulating agent, including interleukins and interferons. Examples of "biomarkers" include but are not limited to IL-2, IL-4, IL-5, IL-8, IL-10, IL-12, IL-13, GM-CSF, IFN-g, and TNF-a. Preferably, biomarkers of the present invention include IL-10, IL-13 and/or IL-1RA. A "biomarker" of the present invention may be detected in a sample.

"Sample" or "a biological sample" refers to cells or component parts, or a fraction or portion thereof of body fluids, including but not limited to blood (e.g., whole blood), amniotic fluid, or cord blood. A "sample" or "biological sample" further refers to plasma, serum, and/or peripheral blood mononuclear cells (PMBC).

In one embodiment, the present invention provides a method of diagnosing susceptibility for preterm delivery in non-pregnant women or pregnant women comprising obtaining a sample from the woman and assaying the sample for the presence or absence of one or more diagnostic biomarkers, where the presence or absence of one or more diagnostic biomarkers is indicative of susceptibility for preterm delivery in the woman. In another embodiment, the sample comprises PMBC supernatant. In another embodiment, the sample comprises whole blood. In another embodiment, the sample comprises serum. In another embodiment, the one or more diagnostic biomarkers comprise a microbial component lipopolysacharide (LPS) or another immune stimulant induced cytokine, cytokine receptor, cytokine receptor antagonist, chemokine, chemokine receptor, and/or chemokine receptor antagonist expression profile. In another embodiment, the one or more diagnostic biomarkers comprise inflammatory and/or anti-inflammatory cytokine. In other embodiments, the one or more diagnostic biomarkers comprise a cytokine receptor, cytokine receptor antagonist, chemokine, chemokine receptor, and/or chemokine receptor antagonist. In another embodiment, the diagnostic biomarkers are analyzed in the presence of cortisol. In another embodiment, the cortisol concentration is in the range of 1 ug/ml to 500 ug/ml, with a preferred range of 1 ug/ml to 150 ug/ml. In another embodiment, the one or more diagnostic biomarkers comprise a low expression of IL-10, IL-13 and/or IL-1RA. In another embodiment, the low expression of IL-10, IL-13 and/or IL-1RA comprises a 1 to 3 fold decrease in expression compared to levels ordinarily found in a healthy individual.

There are many techniques readily available in the field for detecting the presence or absence of a cytokine, cytokine receptor, cytokine receptor antagonist, chemokine, chemokine receptor, and/or chemokine receptor antagonist or other biomarkers, including protein microarrays. For example, some of the detection paradigms that can be employed to this end include optical methods, electrochemical methods (voltometry and amperometry techniques), atomic force microscopy, and radio frequency methods, e.g., magnetic resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry) such as ELISPOT.

Similarly, there are any numbers of techniques that may be employed to isolate and/or fractionate biomarkers. For example, a cytokine, cytokine receptor, cytokine receptor antagonist, chemokine, chemokine receptor, and/or chemokine receptor antagonist may be captured using biospecific capture reagents, such as antibodies, aptamers or antibodies that recognize the biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called "affinity capture mass spectrometry," or "Surface-Enhanced Affinity Capture" or "SEAC," which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer and hybrids of these.

Alternatively, for example, the presence of biomarkers such as a cytokine, cytokine receptor, cytokine receptor antagonist, chemokine, chemokine receptor, and/or chemokine receptor antagonist may be detected using traditional immunoassay techniques. Immunoassay requires biospecific capture reagents, such as antibodies, to capture the analytes. The assay may also be designed to specifically distinguish protein and modified forms of protein, which can be done by employing a sandwich assay in which one antibody captures more than one form and second, distinctly labeled antibodies, specifically bind, and provide distinct detection of, the various forms. Antibodies can be produced by immunizing animals with the biomolecules. Traditional immunoassays may also include sandwich immunoassays including ELISA or fluorescence-based immunoassays, as well as other enzyme immunoassays.

Prior to detection, a cytokine, cytokine receptor, cytokine receptor antagonist, chemokine, chemokine receptor, and/or chemokine receptor antagonist may also be fractionated to isolate them from other components in a solution or of blood that may interfere with detection. Fractionation may include white blood cell isolation from other blood components, sub-cellular fractionation of white blood cell components and/or fractionation of the desired cytokine, cytokine receptor, cytokine receptor antagonist, chemokine, chemokine receptor, and/or chemokine receptor antagonist from other biomolecules found in white blood cells using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

Alternatively, for example, the presence of biomarkers such as a cytokine, cytokine receptor, cytokine receptor antagonist, chemokine, chemokine receptor, and/or chemokine receptor antagonist may be detected using PCR techniques or flow cytometry. All of the available techniques for cytokine, cytokine receptor, cytokine receptor antagonist, chemokine, chemokine receptor, and/or chemokine receptor antagonist detection may be used.

Diagnostic Assays of the Invention

The invention provides various diagnostic assays/tests to predict whether women are at risk of preterm birth.

As described above, in one embodiment of the invention, the diagnostic test comprises drawing blood from a patient, separating the blood cells (for example, separating the peripheral blood mononuclear cells (PBMC)), exposing the separated cells to an antigen (for example, LPS) and assessing the immune response.

In another embodiment, whole blood may be stimulated ex vivo without separating the blood cells. For example, whole blood stimulation may be carried out by drawing blood from the subject into collection tubes coated with an antigen and/or stimulant and allowing it to incubate at 37 degrees Celsius, for a desired amount of time (for example, for 16-24 hours). The immune response may be subsequently assessed by using various techniques known in the art. In one embodiment, after collecting blood from the subject and incubating with it with the antigen and/or stimulant, the collection tubes are centrifuged, the plasma is harvested and assayed for an immune response.

In an embodiment, blood from the subject is drawn into collection tubes coated with antigens as well as into positive and negative control collection tubes. The antigens and/or stimulants induce an immune response, for example by inducing expression of a cytokine, cytokine receptor, cytokine receptor antagonist, chemokine, chemokine receptor, and/or chemokine receptor antagonist. The antigens or stimulants which induce the expression of a cytokine, cytokine receptor, cytokine receptor antagonist, chemokine, chemokine receptor, and/or chemokine receptor antagonist include but are not limited to LPS, cortisol, phytohemagglutinin, maternal histocompatibility antigens, paternal histocompatibility antigens, fetal histocompatibility antigens, other microbial antigens, cytokines, phorbol esters (e.g., phorbol myristate acetate (PMA)), agents that induce Th1 or Th2 type differentiation of lymphocytes singly or combination thereof.

In a further embodiment, the immune response induced by the antigens and/or stimulants may be assessed by assaying the expression of a cytokine, cytokine receptor, cytokine receptor antagonist, chemokine, chemokine receptor, and/or chemokine receptor antagonist. Various techniques may be used to assess the immune response including but not limited to enzyme-linked immunosorbent spot (ELISpot), enzyme-linked immunosorbent assay (ELISA), microarray assay, quantitative PCR, Northern blot assay, Southern blot assay, Western blot assay immunohistochemical assay or binding assay. In a preferred embodiment, ELISpot is used to assess the cytokine expression and/or chemokine expression. These assays may be performed at bedsite/doctors' offices, in a laboratory or during transportation to the laboratory. Antibodies against various cytokine, cytokine receptor, cytokine receptor antagonist, chemokine, chemokine receptor, and/or chemokine receptor antagonist may be used to assess an immune response. These antibodies may be any one or more of a monoclonal antibody or fragment thereof, a polyclonal antibody or a fragment thereof, chimeric antibodies, humanized antibodies, human antibodies and a single chain antibody. In one embodiment, the antibodies may be conjugated with a radiolabel, an enzyme, a chromophore or a fluorophore for immune response detection.

To ascertain whether a woman is at an increased risk of preterm delivery, the aforementioned assays are carried out using blood samples from test subjects who are non-pregnant women and/or pregnant women. The results obtained (for example, the immune response induced which is measured as a function of the expression of a cytokine, cytokine receptor, cytokine receptor antagonist, chemokine, chemokine receptor, and/or chemokine receptor antagonist) from the test subjects are compared to the results obtained from control subjects. In one embodiment, the control subjects are women who delivered at full term. In another embodiment, if the expression level of a cytokine, cytokine receptor, cytokine receptor antagonist, chemokine, chemokine receptor, and/or chemokine receptor antagonist in test subjects is higher or lower than the range of the expression level of the cytokine, cytokine receptor, cytokine receptor antagonist, chemokine, chemokine receptor, and/or chemokine receptor antagonist in the control subjects, the test subject is at an increased risk of preterm delivery.

The invention further provides a diagnostic kit comprising a collection tube coated with an antigen and/or stimulant, a positive control collection tube and/or a negative control collection tube. The kit further comprises reagents to detect an immune response (for example antibodies that bind to a cytokine, cytokine receptor, cytokine receptor antagonist, chemokine, chemokine receptor, and/or chemokine receptor antagonist expressed), for example, antibodies to detect the cytokine, cytokine receptor, cytokine receptor antagonist, chemokine, chemokine receptor, and/or chemokine receptor antagonist, buffers and instructions.

In various embodiments, the invention includes methods of identifying a non-pregnant woman at risk for preterm delivery, comprising: obtaining a sample from the non-pregnant woman, determining the expression level of one or more biomarkers in the sample, and comparing the expression level of the one or more biomarkers with the expression level of biomarkers from those observed in women who delivered fullterm (controls). Since there is individual variation, the control values will constitute a range. If the level of expression of the one or more biomarkers in the sample is higher or lower than the level of expression of the same biomarkers in women who delivered fullterm (outside the range), then it is indicative that the non-pregnant woman is at risk for preterm delivery. Depending on how much the patient biomarker values are outside the range of the standard controls, the risk of preterm delivery may be determined as "low, medium or high." The biomarkers include but are not limited to IL-10, IL-13 and/or IL-1RA. The sample can comprise stimulated PBMC/whole blood supernatant (in the presence or absence of cortisol). Alternatively, the sample can comprise serum.

In various embodiments, the invention includes methods of diagnosing susceptibility of preterm delivery in a woman, comprising: obtaining a sample from the woman, determining the expression level of one or more diagnostic biomarkers in the sample, and comparing the expression level of the one or more biomarkers with the expression level of biomarkers from women who delivered fullterm (normal range). If the level of expression of the one or more diagnostic biomarkers in the sample is higher or lower than the level of expression of the same diagnostic biomarkers in the women who delivered fullterm (normal range), then it is indicative that the woman is at risk for preterm delivery. The diagnostic biomarkers can be inflammatory and/or anti-inflammatory cytokines. In other embodiments, the diagnostic biomarkers can be a cytokine receptor, cytokine receptor antagonist, chemokine receptor, and/or chemokine receptor antagonist. The diagnostic biomarkers selected include but not limited to IL-10, IL-13 and/or IL-1RA. Biomarker expression levels that are at least one to three times less than (or greater than, for other biomarkers) the biomarker expression levels of a control are indicative of preterm delivery. The sample can comprise stimulated PBMC/whole blood supernatant (in the presence or absence of cortisol). Alternatively, the sample can comprise serum. The women may be non-pregnant or pregnant.

The present invention is also directed to a kit for use to determine the risks of preterm delivery. The kit is useful for practicing the inventive method of determining the risk of preterm delivery of non-pregnant or pregnant women. The kit is an assemblage of materials or components, including a diagnostic bioassay of the present invention.

The exact nature of the components configured in the inventive kit depends on its intended purpose. For example, some embodiments are configured for the purpose of diagnosing susceptibility of women for preterm delivery. In one embodiment, the kit is configured particularly for the purpose of determining the risk of preterm delivery of non-pregnant women. In another embodiment, the kit is configured particularly for the purpose of diagnosing susceptibility of women for preterm delivery of pregnant or non-pregnant women.

Instructions for use may be included in the kit. "Instructions for use" typically include a tangible expression describing the technique to be employed in using the components of the kit to effect a desired outcome, such as determine the risks of preterm delivery. Optionally, the kit also contains other useful components, such as, specially prepared test tubes, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a collection tube coated with an antigen and/or a stimulant for use to collect and stimulate a biological sample from a woman. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Biomarker Assay

Peripheral blood mononuclear cells (PBMC) from non-pregnant (at least 5-6 years post-partum) women with history of preterm or full term delivery, in addition to the microbial component lipopolysaccharide (LPS)-induced cytokine expression profile were examined. PBMC were separated from whole blood using Ficoll gradient. The cells were counted and equal numbers of cells were plated in 24 well plates. PBMC were treated with cortisol (50 or 300 ug/ml) or media for 1 hour prior to stimulation with LPS (0, 1, or 100 ug/ml) for 24 hours. The PBMC were lysed and the supernatant was examined for inflammatory and anti-inflammatory cytokine expression by using Bioplex technology (Bio-rad). The inventors found that during the non-pregnant state IL10, IL13 and IL1Ra expression was lower in the PBMC obtained from women whom had previous preterm delivery, and that those biomarkers may be measured to identify women who were at risk for preterm delivery in the future.

In this study two patients were preterm and four were full term. There were 9 samples per patient (3×3 design) and all samples from each patient were analyzed twice for cytokine concentrations with the exception of one full term subject who only had one analysis of each sample. As a result there are a total of 99 observations for each cytokine measured. The assay simultaneously measured concentrations of 11 inflammatory markers: IL-1ra (IL1-receptor antagonist), IL-2, IL-4, IL-5, IL-8, IL-10, IL-12, IL-13, GM-CSF, IFN-g, and TNF-a.

Example 2

Establishment of Cut Off Points

Many samples were above or below the detection for some of the endpoints. Cut off points were established for each cytokine measured (Table 1). If a sample was out of the range of detection, a default value was assigned to the sample as indicated below.

TABLE 1

The establishment of cut off points for out of range values.

| Cytokine | Limit of Detection | Out of Range Set Value | Fraction of Samples out of Detection Range |
|---|---|---|---|
| IL-1ra | all samples within levels of detection | n/a | 0/99 |
| IL-2 | LL = 0.50 | 0.25 | 10/99 |
| IL-4 | LL = 0.14 | 0.08 | 6/99 |
| IL-5 | LL = 0.90 | 0.5 | 82/99 |
| IL-8 | UL = 95,000 | 100,000 | 79/99 |
| IL-10 | all samples within levels of detection | n/a | 0/99 |
| IL-12 | LL = 0.33 | 0.15 | 19/99 |
| IL-13 | LL = 0.17 | 0.08 | 8/99 |
| GM-CSF | LL = 1.18 | 0.60 | 11/99 |
| IFN-g | LL = 1.21 | 0.60 | 5/99 |
| TNF-a | all samples within levels of detection | n/a | 0/99 |

LL = Lower Limit;
UL = Upper Limit

All samples that were below the range of detection for IL-2, IL-4, IL-13, and IFN-g were from the two subjects with a history of preterm delivery. Of the 11 samples assayed that were below detection limits for GM-CSF, only 1 was from a subject with a full-term delivery while the rest were from subjects with histories of preterm deliveries.

Example 3

Statistical Analysis

Empirical means and standard errors for each cytokine and treatment group are presented herein. Here, the averages of replicate measures were calculated first for each subject. The mean and SEM were then taken across each treatment group.

All raw data was tested via the Kolmogorov-Smirnov test to determine if the data followed a normal distribution. Log-transformations were performed for all data found to have a non-normal distribution prior to further statistical analysis. For each cytokine, a mixed effects model was used to examine all data for significant effects with the outcome variable as the cytokine concentration; the fixed predictor variables as LPS concentration, cortisol concentration, and delivery status (pre- or full-term); and the random effect due to the replicate data points. To test the interaction of the three fixed predictor variables on cytokine concentration, both first and second level interactions ware added to each cytokine model. Post-hoc testing was performed using a Student's t-test.

Example 4

Cortisol and LPS Concentrations

All 99 observations were initially used in the analysis to first determine which concentrations of LPS and cortisol induced the most robust effect. For all cytokines measured there was no significant difference between the effects of 1 ug/ml and 100 ug/ml LPS. For several cytokines (IL-1ra, IL-10, and IL-13), 300 ug/ml cortisol had a more significant effect to suppress cytokine levels than 50 ug/ml.

As a result of the findings, the inventors focused on the data with 0 or 300 ug/ml of cortisol pretreatment crossed with 0 or 1 ug/ml LPS. This results in 4 samples per subject, each analyzed twice (with exception of the samples from the full term subject who only had one analysis of each sample). With 8 measurements per subject (with the exception of the full term subject who only has 4 measurements) this results in a data set with 44 measurements for each of the cytokines.

Example 5

Analysis of Testing for Cytokine Differences Between Groups

Using the same mixed model regression, estimated group means and standard errors were calculated. Differences between preterm and full-term pregnancies were considered significant where $p<0.10$.

Based on the results of the statistical modeling, cortisol did suppress secretion of IL-13 and IL-1ra; LPS increased secretion of IL-4, IL-10, IL-13, TNF-a, and IL-1ra; and women who had preterm deliveries had overall lower secretion levels of IL-10, IL-13, and IL-1ra (Table 2).

TABLE 2

Global effects of cortisol, LPS, and premature delivery on cytokine secretion levels in PBMC based on results of mixed modeling.

| Cytokine | Cortisol Effect | LPS Effect | Pre-term Effect |
|---|---|---|---|
| IL-2 | n/c, p = .80 | n/c, p = .50 | n/c, p = .17 |
| IL-4 | n/c, p = .26 | increase, p = .07 | n/c, p = .59 |
| IL-10 | n/c, p = .12 | increase, p = .01 | decrease, p = .01 |
| IL-13 | decrease, p = .01 | increase, p = .04 | decrease, p = .02 |
| IFN-g | n/c, p = .10 | n/c, p = .17 | n/c, p = .22 |
| TNF-a | n/c, p = .41 | increase, p = .04 | n/c, p = .75 |
| GM-CSF | n/c, p = .51 | n/c, p = .19 | n/c, p = .17 |
| IL-1ra | decrease, p = .03 | increase, p = .09 | decrease, p = .01 | n/c = No Change

Women who had preterm deliveries had lower baseline IL-10, IL13 and IL-1Ra expression compared to those who delivered full term. There were no differences in cytokine production between LPS-stimulated PBMC from preterm delivering women when compared with that from women with full-term deliveries. In other words, adjusting for unstimulated secretion levels, the concentration of cytokines released from LPS stimulation was no different between the two groups of women. In the presence of cortisol PBMC from women who had preterm deliveries produced lower IL-13 and IFN-g, expression when compared with that from women with full-term deliveries.

REFERENCES

Hutzal C E, Boyle E M, Kenyon S L, Nash J V, Winsor 5, Taylor D J, Kirpalani H. Use of antibiotics for the treatment of preterm parturition and prevention of neonatal morbidity: a metaanalysis. Am J Obstet Gynecol. 2008 December; 199(6):620.e1-8. Epub 2008 Oct. 30.

Swamy G K, Ostbye T, Skjaerven R. Association of preterm birth with long-term survival, reproduction, and next-generation preterm birth. JAMA. 2008 Mar. 26; 299(12): 1429-36. ERRATUM in: JAMA. 2008 Jul. 9; 300(2): 170-1.

DeFranco E, Teramo K, Muglia L. Genetic influences on preterm birth. Semin Reprod Med. 2007 January; 25(1): 40-51.

Plunkett J, Muglia L J. Genetic contributions to preterm birth: implications from epidemiological and genetic association studies. Ann Med. 2008; 40(3):167-95.

Goldenberg R L, Culhane J F, Iams JD, Romero R. Epidemiology and causes of preterm birth. Lancet. 2008 Jan. 5; 371(9606):75-84.

Blank V, Hirsch E, Challis J R, Romero R, Lye S J. Cytokine signaling, inflammation, innate immunity and preterm labour—a workshop report. Placenta. 2008 March; 29 Suppl A:S102-4.

Mazaki-Tovi S, Romero R, Kusanovic J P, Erez O, Pineles B L, Gotsch F, Mittal P, Than N G, Espinoza J, Hassan S S. Recurrent preterm birth. Semin Perinatol. 2007 June; 31(3):142-58.

Romero R, Espinoza J, Gongalves L F, Kusanovic J P, Friel L, Hassan S. The role of inflammation and infection in preterm birth. Semin Reprod Med. 2007 January; 25(1): 21-39.

Romero R, Espinoza J, Gongalves L F, Kusanovic J P, Friel L A, Nien J K. Inflammation in preterm and term labour and delivery. Semin Fetal Neonatal Med. 2006 October; 11(5):317-26.

Luu T M, Ment L R, Schneider K C, Katz K H, Allan W C, Vohr B R. Lasting effects of preterm birth and neonatal brain hemorrhage at 12 years of age. Pediatrics. 2009 March; 123(3): 1037-44.

Morse S B, Zheng H, Tang Y, Roth J. Early school-age outcomes of late preterm infants. Pediatrics. 2009 April; 123(4):e622-9.

Kamholz K L, Cole C H, Gray J E, Zupancic J A. Cost-effectiveness of early treatment for retinopathy of prematurity. Pediatrics. 2009 January; 123(1):262-9.

Limperopoulos C, Bassan H, Sullivan N R, Soul J S, Robertson R L Jr, Moore M, Ringer S A, Volpe J J, du Plessis A J. Positive screening for autism in ex-preterm infants: prevalence and risk factors. Pediatrics, 2008 April, 121(4):758-65.

Jacobs S E, O'Brien K, Inwood S, Kelly E N, Whyte H E. Outcome of infants 23-26 weeks of gestation pre and post surfactant. Acta Paediatr 2000, 89(8):959-965.

Hack M, Flannery D J, Schluchter M, et al. Outcomes in young adulthood for very-low-birth-weight infants. N Engl J Med 2002, 346(3):149-157.

Genç, M R, Gerber S, Nesin M, Witkin S S. Polymorphism in the interleukin-1 gene complex and spontaneous preterm delivery. Am J Obstet Gynecol. 2002 July; 187(1): 157-63.

Peltier M R. Immunology of term and preterm labor. Reprod Biol Endocrinol. 2003 Dec. 2; 1:122.

Kalish R B, Vardhana S, Gupta M, Pemi S C, Witkin S S, Interleukin-4 and -10 gene polymorphisms and spontaneous preterm birth in multifetal gestations. Am J Obstet Gynecol. 2004 March; 190(3):702-6.

Gotsch F, Romero R, Kusanovic J P, Erez O, Espinoza J, Kim C J, Vaisbuch E, Than N G, Mazaki-Tovi S, Chaiworapongsa T, Mazor M, Yoon B H, Edwin S, Gomez R, Mittal P, Hassan S S, Sharma S. The anti-inflammatory limb of the immune response in preterm labor, intra-amniotic infection/inflammation, and spontaneous parturition at term: a role for interleukin-10. J Matern Fetal Neonatal Med. 2008 August; 21(8):529-47.

Berghella V, Hayes E, Visintine J, Baxter J K. Fetal fibronectin testing for reducing the risk of preterm birth. Cochrane Database Syst Rev. 2008 Oct. 8; (4):CD006843.

Herbst A, Nilsson C. Diagnosis of early preterm labour. BJOG. 2006 December; 113 Suppl 3:60-7. Review. Erratum in: BJOG. 2008 April; 115(5):674-5.

Lockwood C J, Senyei A E, Dische M R. Casal D, Shah K D, Thung S N, Jones L. Deligdisch L, Garite T J. Fetal fibronectin in cervical and vaginal secretions as a predictor of preterm delivery. N Engl J Med. 1991 Sep. 5; 325(10):669-74.

Honest H, Bachmann L M, Gupta J K, Kleijnen J, Khan K S. Accuracy of cervicovaginal fetal fibronectin test in predicting risk of spontaneous preterm birth: systematic review. BMJ. 2002 Aug. 10; 325(7359):301.

Most O, Langer O, Kerner R, David G B, Calderon I. Can myometrial electrical activity identify patients in preterm labor? Am J Obstet Gynecol. 2008 October; 199(4): 378.e1-6.

Menon R. Camargo M C, Thorsen P, Lombardi S J, Fortunato S J. Amniotic fluid interleukin-6 increase is an indicator of spontaneous preterm birth in white but not black Americans. Am J Obstet Gynecol. 2008 January; 198(1):77. e1-7.

Vogel I, Goepfert A R, Thorsen P, Skogstrand K, Hougaard D M, Curry A H, Cliver S, Andrews W W. Early second-trimester inflammatory markers and short cervical length and the risk of recurrent preterm birth. J Reprod Immunol. 2007 October; 75(2):133-40. Epub 2007 Apr. 17.

Kim K W, Romero R, Park H S, Park C W, Shim S S, Jun J K, Yoon B H. A rapid matrix metalloproteinase-8 bedside test for the detection of intraamniotic inflammation in women with preterm premature rupture of membranes. Am J Obstet Gynecol. 2007 September; 197(3): 292.e1-5.

Spong C Y. Prediction and prevention of recurrent spontaneous preterm birth. Obstet Gynecol. 2007 August; 110(2 Pt 1):405-15. Review.

Ghosh G. Breborowicz A, Brazert M, Maczkiewicz M, Kobelski M, Dubiel M, Gudmundsson S. Evaluation of third trimester uterine artery flow velocity indices in relationship to perinatal complications. J Matern Fetal Neonatal Med. 2006 September; 19(9):551-5.

Leitich H. Secondary predictors of preterm labour. BJOG. 2005 March; 112 Suppl 1:48-50. Review.

Challis J R. Maternal corticotropin-releasing hormone, fetal growth, and preterm birth. Am J Obstet Gynecol. 2004 October; 191(4):1059-60.

Heine R P, McGregor J A, Goodwin T M, Artal R, Hayashi R H, Robertson P A, Varner M W. Serial salivary estriol to detect an increased risk of preterm birth. Obstet Gynecol. 2000 October; 96(4):490.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method, comprising:
    obtaining a sample of peripheral blood mononuclear cells (PMBCs) from a woman at a first time, wherein the woman is in a nonpregnant state at the first time and the woman previously had a preterm delivery or a full term delivery;
    stimulating the PMBC sample with phytohemagglutinin (PHA); and
    detecting a secretion level of a combination of cytokines from the stimulated PMBC sample in the woman at the first time, wherein the combination of cytokines comprises all three of IL-10, IL-13, and IL-1RA.

2. The method of claim 1, wherein the PMBC sample is stimulated with PHA in combination with cortisol, lipopolysaccharide (LPS), or a combination of cortisol and LPS.

3. The method of claim 1, wherein the cytokine secretion levels are detected using a technique from the group consisting of enzyme-linked immunosorbent spot (ELISpot), enzyme-linked immunosorbent assay (ELISA), microarray assay, immunohistochemical assay, binding assay and combinations thereof.

4. The method of claim 1, further comprising:
    obtaining a sample of PMBCs from the woman at a second time, wherein the woman is in a pregnant state at the second time and the second time is a point of time after the first time; and
    detecting the secretion level of the combination of cytokines in the woman at the second time, based on the sample of PMBCs from the woman at the second time.

5. A method, comprising:
    obtaining a sample of blood mononuclear cells (PMBCs) from a first woman at a first time, wherein the first woman at the first time is in a nonpregnant state and the woman desires an assessment of her risk for preterm delivery at the first time;
    exposing the sample of PMBCs from the first woman at the first time ex vivo to a stimulant by collecting the sample of the PMBCs from the first woman at the first time into a container with the stimulant, wherein the stimulant is PHA or PHA combined with another stimulant; and
    assessing a secretion level of a combination of cytokines in the sample of PMBCs from the first woman at the first time, wherein the combination of cytokines comprises all three of IL-10, IL-13, and IL-1RA;
    assessing a secretion level of the combination of cytokines in a second woman, wherein the second woman had full-term delivery;

comparing the secretion level of the combination of cytokines in the first woman at the first time to the secretion level of the combination of cytokines in the second woman to determine if the first woman at the first time is at risk for preterm delivery; and determining the first woman at the first time is at risk for preterm delivery at the first time if the secretion level of the combination of cytokines in the first woman at the first time is higher or lower than the secretion level of the combination of cytokines in the second woman.

6. The method of claim 5, wherein PHA combined with another stimulant is PHA combined with cortisol, lipopolysaccharide (LPS), or a combination of cortisol and LPS.

7. The method of claim 5, wherein the cytokine secretion levels are detected using a technique from the group consisting of enzyme-linked immunosorbent spot (ELISpot), enzyme-linked immunosorbent assay (ELISA), microarray assay, immunohistochemical assay, binding assay and combinations thereof.

8. The method of claim 5, further comprising:

obtaining a sample of blood mononuclear cells (PMBCs) from the first woman at a second time, wherein the first woman at the second time is in a pregnant state and the second time is a point of time after the first time; and assessing the secretion level of the combination of cytokines in the sample of PMBCs from the first woman at the second time.

* * * * *